(12) United States Patent
Frijns et al.

(10) Patent No.: US 8,311,649 B2
(45) Date of Patent: Nov. 13, 2012

(54) COCHLEAR LEAD

(75) Inventors: Johannes H. M. Frijns, Leiderdorp (NL); Janusz A. Kuzma, Parker, CO (US); Jeroen Johannes Briaire, Leiderdorp (NL)

(73) Assignee: Advanced Bionics, Valencia, CA (US)

( * ) Notice: Subject to any disclaimer, the term of this patent is extended or adjusted under 35 U.S.C. 154(b) by 259 days.

(21) Appl. No.: 11/138,146

(22) Filed: May 26, 2005

(65) Prior Publication Data
US 2005/0267558 A1    Dec. 1, 2005

Related U.S. Application Data

(60) Provisional application No. 60/574,473, filed on May 26, 2004.

(51) Int. Cl.
*A61N 1/04* (2006.01)
(52) U.S. Cl. .............. 607/137; 607/56; 607/57; 607/55
(58) Field of Classification Search .................. 607/137, 607/55–57
See application file for complete search history.

(56) References Cited

U.S. PATENT DOCUMENTS

| | | | |
|---|---|---|---|
| 4,819,647 A | 4/1989 | Byers et al. | |
| 5,545,219 A * | 8/1996 | Kuzma | 623/10 |
| 5,603,726 A | 2/1997 | Schulman et al. | |
| 5,645,585 A | 7/1997 | Kuzma | |
| 5,999,859 A * | 12/1999 | Jolly | 607/137 |
| 6,038,484 A | 3/2000 | Kuzma | |
| 6,070,105 A | 5/2000 | Kuzma | |
| 6,078,841 A | 6/2000 | Kuzma | |
| 6,119,044 A * | 9/2000 | Kuzma | 607/137 |
| 6,125,302 A * | 9/2000 | Kuzma | 607/137 |
| 6,129,753 A | 10/2000 | Kuzma | |
| 6,144,883 A | 11/2000 | Kuzma | |
| 6,163,729 A | 12/2000 | Kuzma | |
| 6,195,586 B1 | 2/2001 | Kuzma | |
| 6,304,787 B1 | 10/2001 | Kuzma | |
| 6,321,125 B1 | 11/2001 | Kuzma | |

(Continued)

FOREIGN PATENT DOCUMENTS

WO    03/070133 A1    8/2003

(Continued)

OTHER PUBLICATIONS

Nearly. (n.d.). Roget's 21st Century Thesaurus, Third Edition and Roget's II: The New Thesaurus, Third Edition. Retrieved Apr. 7, 2009, from Thesaurus.com website: http://thesaurus.reference.com/browse/nearly.

*Primary Examiner* — Niketa Patel
*Assistant Examiner* — Joseph Stoklosa
(74) *Attorney, Agent, or Firm* — Steven L. Nichols; Van Cott, Bagley, Cornwall & McCarthy P.C.

(57) ABSTRACT

An electrode array design is provided which is intended for deep insertion into a human cochlea. The distal most portion of the lead can be very thin and flexible and have a wider arc than the remainder of the curved electrode array portion of the lead, which has a more aggressive arc. As a result, the distal most portion of the electrode array can be laterally positioned in a selected cochlear duct, whereas, concurrently, the remaining, more proximal part of the electrode array may be positioned medially (perimodiolar) within the cochlear duct.

23 Claims, 3 Drawing Sheets

U.S. PATENT DOCUMENTS

| | | |
|---|---|---|
| 6,397,110 B1 | 5/2002 | Kuzma |
| 6,411,855 B1 * | 6/2002 | Peeters et al. .................. 607/57 |
| 6,421,569 B1 | 7/2002 | Treaba et al. |
| 6,498,954 B1 | 12/2002 | Kuzma et al. |
| 6,604,283 B1 | 8/2003 | Kuzma |
| 6,862,805 B1 | 3/2005 | Kuzma et al. |
| 6,968,238 B1 | 11/2005 | Kuzma |
| 7,315,763 B2 | 1/2008 | Kuzma et al. |
| 7,319,906 B2 | 1/2008 | Kuzma et al. |
| 7,367,992 B2 | 5/2008 | Dadd |
| 7,406,352 B2 | 7/2008 | Gibson |
| 7,451,000 B2 | 11/2008 | Gibson et al. |
| 7,941,228 B2 | 5/2011 | Kuzma et al. |
| 2004/0127968 A1 * | 7/2004 | Kuzma et al. ................. 607/137 |
| 2004/0220651 A1 | 11/2004 | Kuzma et al. |
| 2004/0243212 A1 | 12/2004 | Dadd et al. |
| 2006/0085055 A1 | 4/2006 | Dadd et al. |

FOREIGN PATENT DOCUMENTS

| | | |
|---|---|---|
| WO | 2004/026199 A2 | 4/2004 |
| WO | 2004/026199 A3 | 4/2004 |

* cited by examiner

COCHLEAR LEAD

The present application claims the benefit of U.S. Provisional Patent Application Ser. No. 60/574,473, filed 26 May 2004, which application is herein incorporated by reference in its entirety.

BACKGROUND OF THE INVENTION

The present invention relates to implantable stimulation devices, and, more particularly, to electrode arrays for stimulation of the cochlea. Electrode arrays consist of electrode contacts generally placed along one side of an elongate carrier so that when the array is implanted within one of the cochlear ducts such as the scala tympani, the electrode contacts are positioned in close proximity to the cells that are to be stimulated, allowing such cells to be stimulated with minimal power consumption.

For purposes of clarity, as used herein, an implantable stimulating lead is a device that has one or more electrode contacts that deliver current to tissue to be stimulated. An electrode contact is that part of the stimulating device which is actually electrically conductive and is in contact with the body tissue that is to be stimulated. The term "electrode" may be used narrowly as the electrode contact or contacts only and, other times, more broadly, as the electrode contact or contacts and all the surrounding structure, including the insulation carrier that the contacts are placed upon, as well as the conductor wires and any other assemblies within or on the insulation carrier. As used herein, the broad definition of the term "electrode" will be adopted, which definition includes the electrode contacts and all surrounding structures. In addition, when the term "lead" is used, it will refer herein to the entire elongate structure and will include the part that is the "electrode." The term "electrode array" will refer to that portion of the lead that includes all of the electrode contacts.

Hearing loss, which may be due to many different causes, is generally of two types: conductive and sensorineural. Of these, conductive hearing loss occurs where the normal mechanical pathways for sound to reach the hair cells in the cochlea are impeded, for example, from damage to the ossicles. Conductive hearing loss may often be helped by using conventional hearing aids that amplify sounds so that acoustic information can reach the cochlea and the hair cells. Some types of conductive hearing loss are also amenable to alleviation by surgical procedures.

In many people who are profoundly deaf, however, the reason for their deafness is sensorineural hearing loss. This type of hearing loss can arise from the absence or the destruction of the hair cells in the cochlea which transduce acoustic signals into auditory nerve impulses. Individuals with sensorineural hearing loss are unable to derive any benefit from conventional hearing aid systems no matter how loud the acoustic stimulus is, because the mechanism for transducing sound energy into auditory nerve impulses has been damaged. Thus, in the absence of properly functioning hair cells, auditory nerve impulses cannot be generated directly from sounds.

To overcome sensorineural deafness, cochlear implant systems or cochlear prostheses have been developed, which can bypass the hair cells located in the vicinity of the radially outer wall of the cochlea by presenting electrical stimulation to the auditory nerve fibers directly. This leads to the perception of sound in the brain and provides at least partial restoration of hearing function. Thus, most of these cochlear prosthesis systems treat sensorineural deficit by stimulating the ganglion cells in the cochlea directly using an implanted electrode or lead that has an electrode array.

A cochlear prosthesis operates by directly stimulating the auditory nerve cells, bypassing the defective cochlear hair cells that normally transduce acoustic energy into electrical activity to the connected auditory nerve cells. In addition to stimulating the nerve cells, the electronic circuitry and the electrode array of the cochlear prosthesis separate the acoustic signal into a number of parallel channels of information, each representing a narrow band of frequencies within the perceived audio spectrum. Ideally, each channel of information should be conveyed selectively to a subset of auditory nerve cells that normally transmits information about that frequency band to the brain. Those nerve cells are arranged in an orderly tonotopic sequence, from the highest frequencies at the basal end of the cochlear spiral to progressively lower frequencies towards the apex. In practice, however, this goal can be difficult to realize because of the particular anatomy of the cochlea.

Over the past several years, a consensus has generally emerged that the scala tympani, one of the three parallel ducts that make up the spiral-shaped cochlea, provides the best location for implantation of an electrode array used as part of a cochlear prosthesis. The electrode array to be implanted in the scala tympani typically can consist of a thin, elongated, flexible carrier containing several longitudinally disposed and separately connected stimulating electrode contacts, conventionally numbering about 6 to 30. Such an electrode array is pushed into the scala tympani duct in the cochlea to a depth of about 20-30 mm via a surgical opening made in the round window at the basal end of the duct.

In use, the cochlear electrode array delivers electrical current into the fluids and tissues immediately surrounding the individual electrode contacts to create transient potential gradients that, if sufficiently strong, cause the nearby auditory nerve fibers to generate action potentials. The auditory nerve fibers branch from cell bodies located in the spiral ganglion which lies in the bone or modiolus, adjacent to the inside wall of the scala tympani. Because the density of electrical current flowing through volume conductors such as tissues and fluids tends to be highest near the electrode contact that is the source of such current stimulation at one contact site tends to selectively activate those spiral ganglion cells and their auditory nerve fibers that are closest to that contact site. Thus, it is important generally for the electrode contacts to be positioned as close to the ganglion cells as possible. Conventionally, after implant, the electrode array consisting of electrode contacts should hug the modiolar wall (or inside wall of the scala tympani). When the electrode side of the array is positioned closest to the modiolar wall, the electrode contacts are on the medial side of the lead.

In order to address the above need, it is known in the art to make an intracochlear electrode array that includes a spiral-shaped, resilient carrier which generally has a natural, spiral shape so that the array better conforms to the shape of the scala tympani. See, e.g., U.S. Pat. No. 4,819,647, which is incorporated herein by reference. While the electrode array with a spiral-shaped carrier shown in the '647 patent represents a significant advance in the art, it lacks sufficient shape memory to allow it to return to its original curvature (once having been straightened for initial insertion) and to provide sufficient hugging force to wrap snugly against the modiolus of the cochlea.

It is also known in the art, as shown in U.S. Pat. Nos. 5,545,219 and 5,645,585, to construct an electrode carrier from two initially straight members, a rod-like electrode carrier and a flexible rod-like positioning member. The '219 and '585 U.S. patents are also incorporated herein by reference. As shown in these patents, the two members extend in substantially parallel relation to and closely alongside each other, but are connected to each other only at their respective leading and trailing ends. After implant, a pushing force is applied to the positioning member so that it is forced to assume an outwardly arched configuration relative to the electrode carrier, thereby forcing the electrode carrier into a close hugging engagement with the modiolus and placing the electrode contacts as close to the cells of the spiral ganglion as possible. The '219 patent, in particular, shows in FIGS. 1-10 and describes in the accompanying text an excellent summary of prior art electrodes and the deficiencies associated therewith. Other patents relevant to the subject matter of cochlear stimulation leads are: U.S. Pat. Nos. 6,125,302; 6,070,105; 6,038,484; 6,144,883; and 6,119,044, which are all herein incorporated by reference.

While the electrode arrays taught in the above-referenced '219 and '585 patents are based on the correct goal, i.e., to force the electrode carrier into a close hugging engagement with the modiolus, it does so by using an additional element that makes lead manufacture more difficult and expensive.

An electrode design for a cochlear application is disclosed in U.S. patent application Ser. No. 10/666,465, filed Sep. 19, 2003, now U.S. Pat. No. 7,315,763, which application is herein incorporated by reference in its entirety.

There is a need to have an improved cochlear electrode/lead that is easily implanted and provides superior cochlear electrical stimulation.

SUMMARY OF THE INVENTION

The present invention addresses the above and other needs by providing a cochlear lead that fulfills the above needs.

In one embodiment of the present invention, an implantable cochlear lead is provided for delivering electrical stimulation to cochlear ganglion cells.

The cochlear lead may comprise: a plurality of electrode contacts embedded at the distal end of the lead, wherein the length of cochlear lead encompassing the plurality of electrode contacts defines an electrode array. The electrode array may be divided into a proximal portion and a distal portion. The distal portion of the electrode array can be configured and dimensioned to provide a lateral placement position within a selected cochlear duct and the proximal portion of the electrode array can be configured and dimensioned to provide a perimodiolar (medial) placement position within the selected cochlear duct.

In another embodiment of the cochlear lead, the distal portion of the electrode array may have cross-sectional areas that are substantially or significantly smaller than the corresponding spaces of the selected cochlear duct, which duct is preferably the scala tympani. This facilitates the distal portion of the electrode array to assume a position closer to the lateral wall of the cochlea (lateral position) within the selected cochlear duct, e.g., the scala tympani.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The cochlear lead of the present invention may be used with an implantable multi-channel pulse generator, e.g., an implantable cochlear stimulator (ICS) of the type disclosed in U.S. Pat. No. 5,603,726, incorporated herein by reference in its entirety or with other suitable stimulators.

Figure 1:
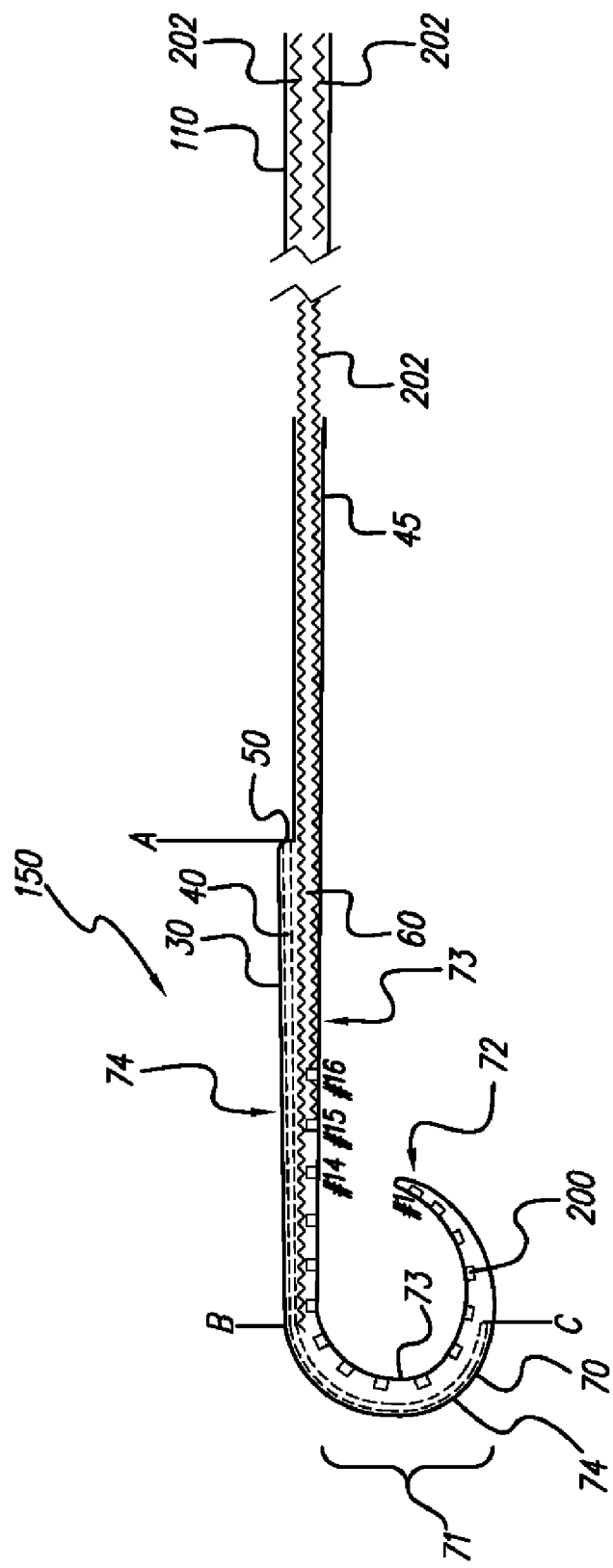
FIG. 1 shows, in accordance with the present invention, an illustration of one embodiment of the cochlear lead with an electrode array designed for placement into a chamber or duct of the cochlea, e.g., the scala tympani.

FIG. 1 shows an embodiment of the lead 150, in accordance with the present invention. The electrode contacts 200 are spaced apart along the medial side of the lead, which side is on the inside of the curvature of the curved electrode array. In the lead embodiment shown, the electrode contacts in the electrode array are positioned "in-line" to the lead, meaning that the electrode contacts are spaced apart more or less in alignment with the lead axis. To have an in-line configuration of electrode contacts, a straight alignment is not necessary. Rather, "in-line" shall mean, as used herein, two or more electrodes placed linearly, including possibly, a curved line, such that one electrode contact is placed more distal on the lead to another electrode contact.

Figure 2:
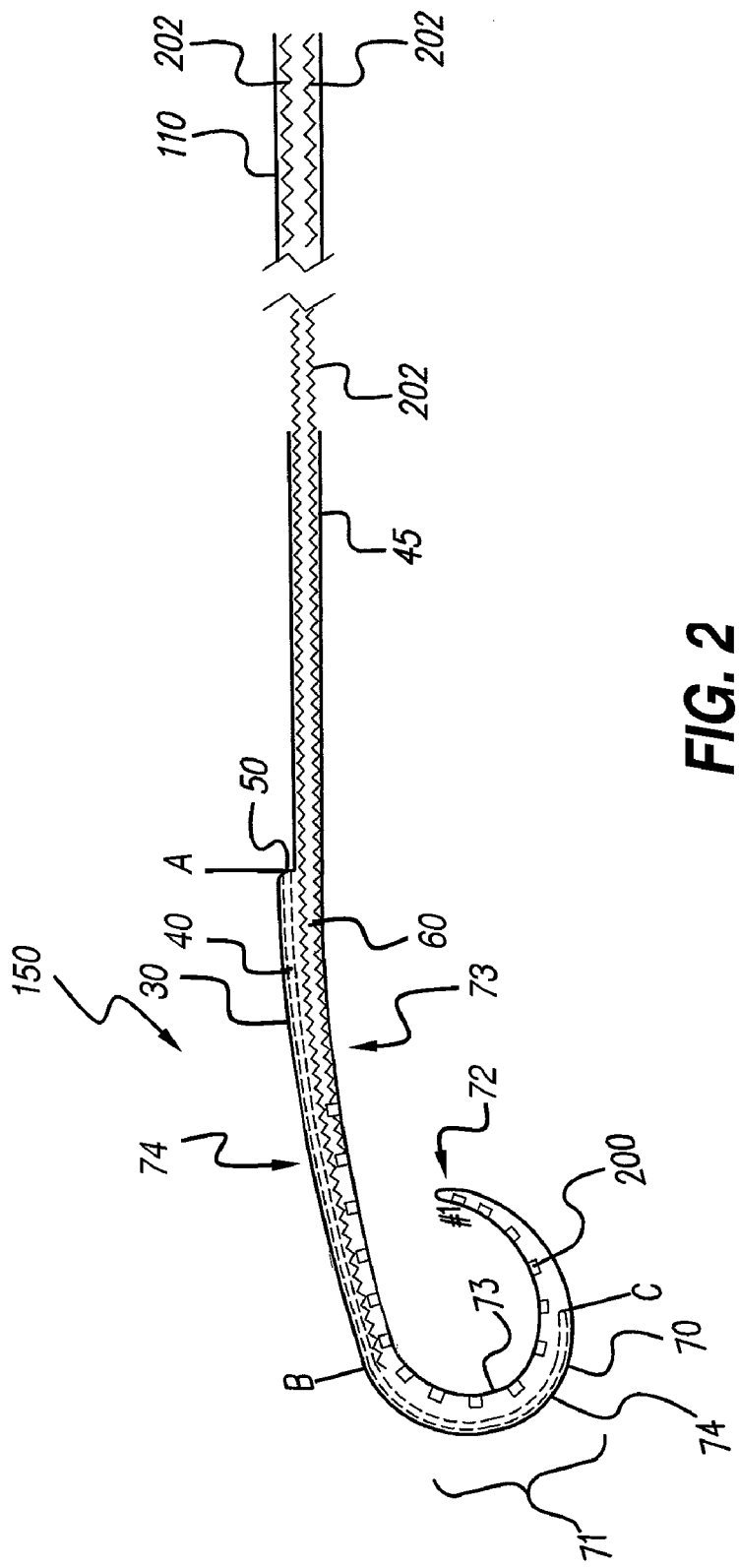
FIG. 2 shows, in accordance with the present invention, an illustration of another embodiment of the cochlear lead with an electrode array having a slightly curved proximal portion.
Figure 3:
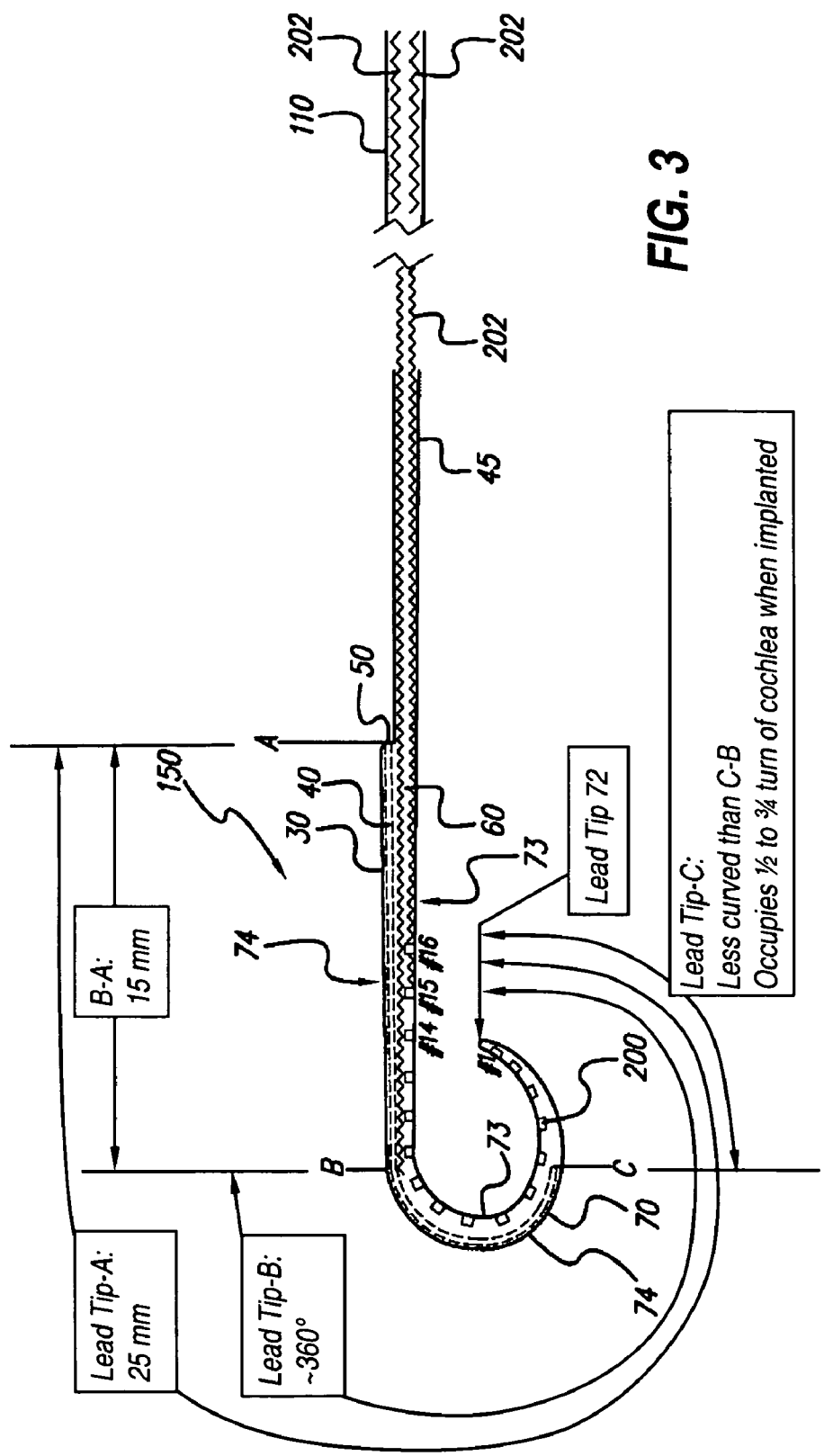
FIG. 3 shows, in accordance with the present invention, an illustration of an embodiment of the cochlear lead with illustrative dimensions.

The lead 150 has an outer (lateral) surface 74, a medial surface 73, opposite the lateral surface 74, which medial surface may contact the modiolus in the cochlea, and a distal lead tip 72. The lead may have nearly a 360° curvature at the distal portion of the lead 70 (beyond point B to the distal tip 72). The lead, beyond Point C of the lead, is intended to be implanted in the cochlea with about one-half to about three-fourths of a full turn. The lead is comprised of an electrode array 70 that has a plurality of spaced-apart electrode contacts 200, a lead section 30 shown as between point A and point B in FIG. 1 (the proximal portion of the electrode array), which lead section may be substantially straight as shown in FIG. 1 or slightly curved as shown in FIG. 2. This lead section 30, which is referred to as the "substantially straight section," shall include all lead embodiments that are in fact straight, as well as those leads which, in lead section 30, are slightly curved.

A thin lead section 45 of the lead, shown in FIG. 1 as right of point A on the lead and a thicker, more proximal lead portion 110 may carry a plurality of conductor wires 202 for connection to an implantable, multi-channel stimulator or to an ICS which can be inductively powered through the skin. The thin, lead section 45 may be thinner than the substantially straight or slightly curved section 30 which may be thicker to accommodate the stylet insertion channel 40. The distal curved part 71 of the lead 150, straightens when a stylet is inserted into the stylet channel 40. As the stylet is withdrawn, the curved parts of the lead, being formed from a material having memory, tends to returns to its original curved position and helps the electrode contacts 200 maintain a final, stable position after implantation.

Some representative dimensions of the lead 150 can be as follows. The substantially straight section 30 can be about 15 millimeters long. This substantially straight section 30, combined with the length of the rest of electrode array 70, may be about 25 millimeters long. The thicker portion of the electrode array section between Point B and C could be between about 3.0 millimeters in diameter plus or minus 0.5 millimeters. The distal portion of the electrode array at Point C to the distal tip 72 of the lead can be much smaller, and typically is significantly smaller dimensionally than the cochlear duct space in which the distal portion of the electrode array is to be placed. It is emphasized that the dimensions recited are merely example embodiments of the invention and other dimensions may be used that fall within the scope of the invention.

The profile of the lead 150 along its length can vary, as shown in FIG. 1. For example, the distal portion of the electrode array 70, i.e, from Point C to the lead tip 72, may be tapered. Such tapering accommodates the natural, tapered shape of the scala tympani wherein the electrode array 70 is to be inserted. The lead 150 may have a stylet insertion channel 40 with a channel opening 50. The channel 40 can extend through the substantially straight section 30 of the lead 150 and proceed into the curved part of the lead until Point C, but generally, no further beyond since the overall smaller dimensions (thicknesses or cross-sections) cannot accommodate a channel.

The insulative covering/carrier 60 which forms the body of the lead and provides a covering over the conductor wires 202 can be made from silicone, polyurethanes or other body-compatible, polymeric insulating materials. The type and hardness of the insulative carrier 60 can be selected to provide a specific, desired compliance to the lead body in combination with the compliance of the conductor wires and choice of structures incorporated into the lead 150, e.g., the stylet insertion channel 40.

The carrier/covering material is molded to assume a specific pre-curved shape having memory. Therefore, the natural resting position of the lead has a curved electrode array 70. When the electrode array portion of the lead is straightened by inserting a relatively stiff stylet into the stylet insertion channel 40, the carrier/covering 60 in the curved electrode array, as well as the slightly curved section 30 of the lead 150, stores elastic energy which exerts a contractive force tending to restore the lead to its originally molded curved shape. The lead embodiment in FIG. 1 may preferably have a spiral or helical curve at the distal end of the lead, which distal end can provide up to a nearly 360° circular loop.

When such a lead is implanted, the thicker proximal portion of the electrode array will take a perimodiolar position—that is, with medially oriented electrode contacts 200 on the lead 150 in close proximity to the medial wall of the scala tympani. The most distal part of the lead, i.e., Point C to lead tip 72, however, may be less curved, that is, have a larger radius of curvature, than the electrode array portion from Point B to Point C, which has a smaller radius of curvature. Thus, as the lead 150 is implanted into a cochlear chamber, e.g., the scala tympani, the distal tip 72 of the lead tends to scrape more on the lateral side of the scala tympani wall. As such, after implant, the distal portion of the electrode array 70 is laterally positioned in the cochlear duct, e.g., the scala tympani.

The stylet channel 40 may extend from Point A through much of the lead carrier 30, but can stop short at Point C. The stylet channel depicted in FIG. 1 stops at Point C because, beyond that point, it is preferably to have an extremely thin, flexible tip. The thin tip, for example, from Point C to distal lead tip 72 may have a cross-section or thickness that is significantly smaller than the selected cochlear duct in order to facilitate a lateral positioning of the distal portion of the electrode array within the cochlear duct, after implantation.

The electrode array, when implanted, may turn inside the cochlea from between about 1.25 to about 2.0 turns. The distal portion of the electrode array, which may have about three, four or five electrode contacts in a sixteen electrode contact array embodiment, is preferably very narrow, tapered and flexible. A representative embodiment of the distal portion of the electrode array may provide between about 0.75 to about 1.25 turns in the selected cochlear duct, e.g., scala tympani. This particular tapered shape accommodates the tight curvature and narrower passageway proceeding into the duct of the scala tympani, particularly in the second turn. The tapered portion of the array having electrode contacts #1 to #5 can be extremely flexible, in part, owing to the thinness of the portion and/or, by selecting a compliant carrier material. It is emphasized that the tapered lead tip may have any number of electrode contacts, e.g., numbering between one to five.

In use, the distal portion of the electrode array, for example, from Point C to the distal lead tip 72, shown in FIG. 1, will tend to abut against the outer (lateral) wall in the scala tympani while the array is being inserted and after implantation. The distal end of the lead has a less aggressive curvature compared to the rest of the curved portion of the electrode array 70. The contact pressure applied by the lead tip 72 is towards the lateral, not medial, cochlear wall. However, the thicker, proximal portion of the electrode array between Points A and B will tend to put the electrode contacts in a perimodiolar (medial) position close to the targeted ganglion cells.

At the end of the first turn and the whole of the second turn in the scala tympani, the diameter of the modiolus becomes so small (1.0-1.5 mm) that close positioning of the electrode contacts can produce undesirable cross-stimulation of ganglion cells. In order to reduce this effect, the electrode contacts are kept as far away from the ganglion cells as possible. This is achieved by minimizing the thickness or cross-section of the distal portion of the electrode array, beyond Point C to lead tip 72. Preferably, the distal portion of the array will have a thickness or cross-section that is much smaller than the cochlear duct, e.g., the scala tympani, wherein the distal tip of the lead is placed within. The thin lead tip tends to effectuate a lateral wall lead placement of the distal portion of the electrode array. In contrast, the thicknesses of the lead, for example, between Point A to Point B, is dimensioned to preferably provide a snug fit within the cochlear duct in order to effectuate a periomodiolar (medial) lead placement.

In sum, the lead (electrode array) design of FIG. 1 is a partially perimodiolar design for providing medial lead positioning at the proximal portion of the electrode array and, concurrently, a lateral lead positioning at the distal portion of the electrode array.

While the invention herein disclosed has been described by means of specific embodiments and applications thereof, numerous modifications and variations could be made thereto by those skilled in the art without departing from the scope of the invention set forth in the claims.

What is claimed is:

1. An implantable cochlear lead having a distal lead tip, comprising:
   an electrode array comprising a multiplicity of electrodes spaced apart along the array, said electrode array comprising:
      a first electrode array portion extending from the distal lead tip to a point C on the lead and including a first plurality of the electrodes;

a second electrode array portion extending from point C proximally to a point B on the lead and including a second plurality of the electrodes;

a third electrode array portion extending from point B proximally to a point A on the lead and including a third plurality of the electrodes; and a stylet insertion channel comprising a lumen having an open proximal end and a closed distal end and extending longitudinally through the third and second electrode array portions but not extending into the first electrode array portion, wherein the stylet insertion channel is configured for inserting and withdrawing a stylet during surgery, through the open proximal end of the lumen, to straighten the third and second electrode array portions to facilitate lead implantation;

wherein the second electrode array portion has a smaller radius of curvature than that of the first electrode array portion and than that of the third electrode array portion when the lead is in its relaxed condition without a stylet inserted.

2. The lead of claim 1, wherein the third electrode array portion is straight.

3. The lead of claim 1, wherein the third electrode array portion is slightly curved.

4. The lead of claim 1, wherein the third electrode array portion is about 15 mm long.

5. The lead of claim 1, wherein the first plurality and second plurality of electrodes are on the inside of the curve formed by the electrode array.

6. The lead of claim 1, wherein the first plurality of the electrodes comprises between 3 and 5 of the electrodes.

7. An implantable cochlear lead having a distal lead tip, comprising:

an electrode array comprising a multiplicity of electrodes spaced apart along the array, said electrode array comprising:

a first curved electrode array portion extending from the distal lead tip to a point C on the lead and including a first plurality of the electrodes and configured and dimensioned to provide a lateral placement position within a selected cochlear duct; and a second electrode array portion extending from point C proximally to a point B on the lead including a second plurality of the electrodes, having a smaller radius of curvature than that of the first electrode array portion when the lead is in its relaxed condition without a stylet inserted, and configured and dimensioned to provide a perimodiolar placement position within the selected cochlear duct.

8. The lead of claim 7, wherein the first plurality of electrodes comprises between 3 and 5 of the electrodes.

9. The lead of claim 7, wherein the first electrode array portion is thinner than the second electrode array portion.

10. The lead of claim 7, wherein the first electrode array portion is configured to provide between about 0.5 and about 0.75 turns in a cochlear duct when the distal lead tip is positioned to a depth of 20 to 30 mm inside the duct.

11. The lead of claim 7, wherein the first plurality and second plurality of electrodes are on the inside of the curve formed by the electrode array.

12. The lead of claim 7, further comprising a longitudinal stylet insertion channel comprising a lumen having an open proximal end and a closed distal end and extending through the second electrode array portion, wherein the stylet insertion channel is configured for inserting and withdrawing a stylet during surgery, through the open proximal end of the lumen, to straighten the second electrode array portion to facilitate lead implantation.

13. The lead of claim 12, wherein the stylet insertion channel does not extend into the first electrode array portion.

14. An implantable cochlear lead having a distal lead tip, comprising:

an electrode array comprising a multiplicity of electrodes spaced apart along the array, said electrode array comprising:

a first electrode array portion extending from the distal lead tip to a point C on the lead and including a first plurality of the electrodes;

a second electrode array portion extending from point C proximally to a point B on the lead and including a second plurality of the electrodes and having a smaller radius of curvature than that of the first electrode array portion when the lead is in its relaxed condition without a stylet inserted; and a longitudinal stylet insertion channel comprising a lumen having an open proximal end and a closed distal end and extending through the second electrode array portion but not extending into the first electrode array portion, wherein the stylet insertion channel is configured for inserting and withdrawing a stylet during surgery, through the open proximal end of the lumen, to straighten the second electrode array portion to facilitate lead implantation.

15. The lead of claim 14, wherein the first plurality of electrodes comprises between 3 and 5 of the electrodes.

16. The lead of claim 14, wherein the first electrode array portion is thinner than the second electrode array portion.

17. The lead of claim 14, wherein the first electrode array portion and second electrode array portion together extend nearly 360°.

18. The lead of claim 14, wherein the first electrode array portion is configured to provide between about 0.5 and about 0.75 turns in a cochlear duct when the distal lead tip is positioned to a depth of 20 to 30 mm inside the duct.

19. The lead of claim 14, wherein the electrode array further comprises:

a third electrode array portion extending from point B proximally to a point A on the lead, wherein the third electrode array portion is substantially straight.

20. The lead of claim 14, wherein the first plurality and second plurality of electrodes are on the inside of the curve formed by the electrode array.

21. An implantable cochlear lead having a distal lead tip, comprising:

an electrode array comprising a multiplicity of electrodes spaced apart along the array, said electrode array comprising:

a first electrode array portion extending from the distal lead tip to a point C on the lead and including a first plurality of the electrodes and configured and dimensioned to provide a lateral placement position within a selected cochlear duct; and a second electrode array portion including a second plurality of the electrodes, wherein when the lead is in its relaxed condition without a stylet inserted, the second electrode portion extends from point C proximally to a point B on the lead, has a smaller radius of curvature than that of the first electrode array portion, and is configured and dimensioned to provide a perimodiolar placement position within the selected cochlear duct.

22. The lead of claim 21, further comprising a longitudinal stylet insertion channel comprising a lumen having an open proximal end and a closed distal end and extending through the second electrode array portion, wherein the stylet insertion channel is configured for inserting and withdrawing a stylet during surgery, through the open proximal end of the lumen, to straighten the second electrode array portion to facilitate lead implantation.

23. The lead of claim 22, wherein the stylet insertion channel does not extend into the first electrode array portion.

* * * * *